(12) United States Patent
Kahn et al.

(10) Patent No.: US 7,238,260 B2
(45) Date of Patent: Jul. 3, 2007

(54) PURIFICATION OF N-(2-HYDROXYETHYL)-2-PYRROLIDONE

(75) Inventors: Andrew P. Kahn, Eagleville, PA (US); David W. Leyshon, West Chester, PA (US); Shaw-Chan Lin, West Chester, PA (US); Edward P. Carey, Atglen, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 494 days.

(21) Appl. No.: 10/973,151

(22) Filed: Oct. 26, 2004

(65) Prior Publication Data

US 2006/0086602 A1    Apr. 27, 2006

(51) Int. Cl.
    *B01D 3/14*    (2006.01)
(52) U.S. Cl. ............... 203/74; 203/80; 203/99; 203/DIG. 19
(58) Field of Classification Search ............... None
    See application file for complete search history.

(56) References Cited

U.S. PATENT DOCUMENTS 6,726,811 B2    4/2004    Ugamura et al.

*Primary Examiner*—Tam M. Nguyen
(74) *Attorney, Agent, or Firm*—William C. Long

(57) ABSTRACT

N-(2-hydroxyethyl)-2-pyrrolidone (HEP) is purified by a distillation sequence in which the purified HEP is recovered as a side stream without being separated as an overhead at any point in the procedure.

4 Claims, 3 Drawing Sheets

PURIFICATION OF N-(2-HYDROXYETHYL)-2-PYRROLIDONE

BACKGROUND OF THE INVENTION

1. Field of the Invention

The present invention relates to a method of purifying N-(2-hydroxyethyl)-2-pyrrolidone (herein HEP) by an improved distillation procedure which avoids separating HEP as an overhead distillate stream during the procedure.

2. Description of the Prior Art

HEP is an important chemical of commerce which is primarily useful for the production of N-vinyl-2-pyrrolidone by intermolecular dehydration, the N-vinyl-2-pyrrolidone having utility in the cosmetics, food additives and pharmaceutical industries.

An extensive description of the known procedures for producing and purifying HEP can be found in U.S. Pat. No. 6,726,811, the disclosure of which is incorporated herein in its entirety.

In the procedure described in U.S. Pat. No. 6,726,811, HEP of high purity is recovered from the reaction liquid resulting from reacting gamma-butyrolactone with 2-aminoethanol and which contains N-(2-hydroxyethyl)-2-pyrrolidone, low-boiling component and high-boiling component.

In the process of the reference, the reaction mixture is first distilled in column 1 to separate as overhead a lighter stream containing both light impurities and HEP from a heavier stream containing higher boiling components. The overhead stream from column 1 is then passed to one (FIG. 1) or two (FIG. 2) columns for ultimate recovery of purified HEP.

It has now been found that the distillation recovery of high purity HEP can be significantly enhanced by an improved distillation sequence as provided in accordance with the present invention.

BRIEF DESCRIPTION OF THE INVENTION

In accordance with the present invention, highly purified HEP is recovered from reaction mixtures containing the same by a distillation sequence which avoids separating a HEP stream at any point as an overhead distillate.

DETAILED DESCRIPTION

In contrast to the prior art such as U.S. Pat. No. 6,726,811, in practice of the instant invention improved results are achieved where the primary HEP stream to be purified is not a stream which has previously been recovered as distillate overhead.

Figure 1:
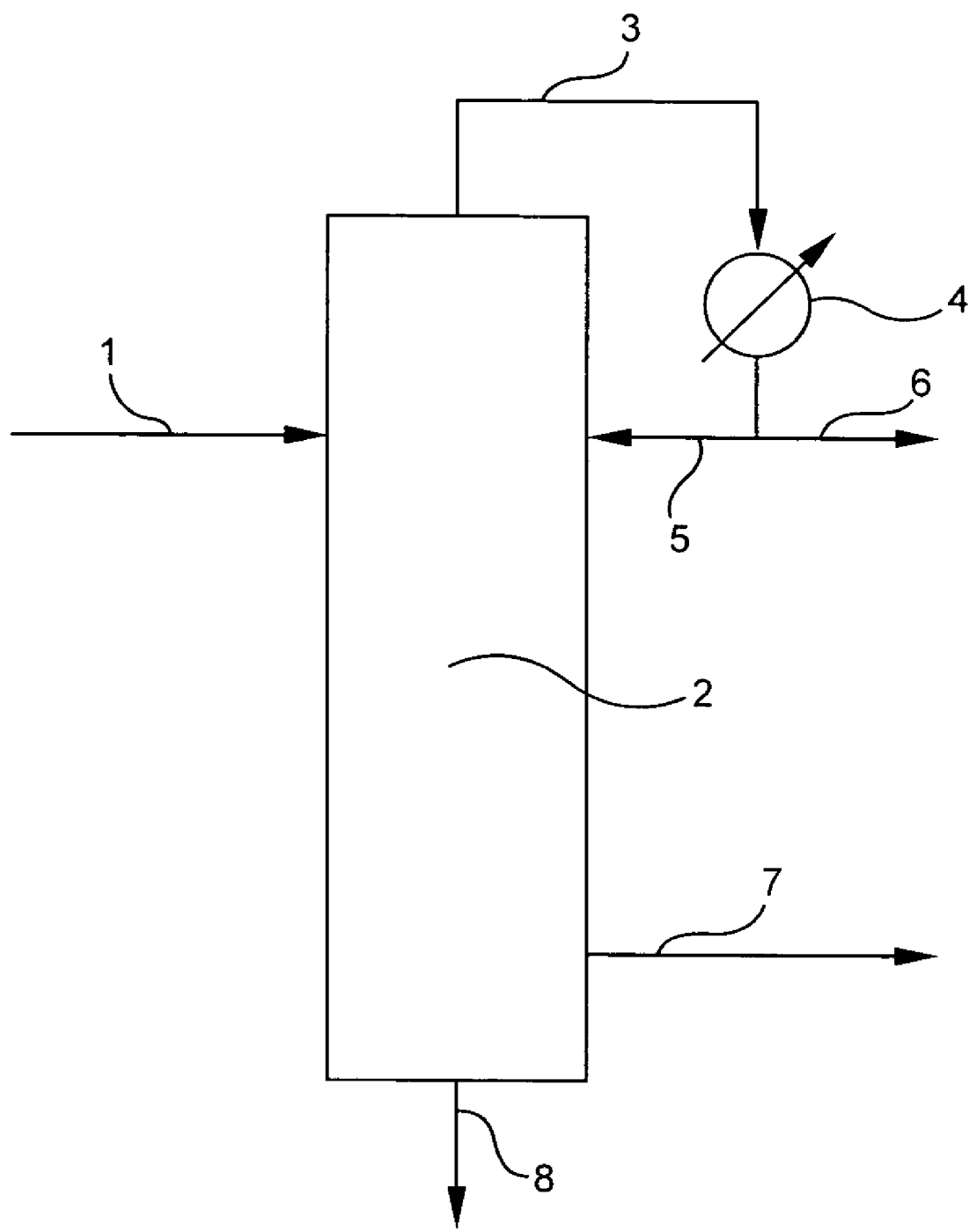
FIG. 1 schematically represents a practice of the invention.

In the practice of the invention using a single fractional distillation column, satisfactory HEP is recovered as a side stream draw off. Referring to FIG. 1, the reaction mixture from the HEP forming procedure is fed via line 1 to distillation column 2 at an intermediate point. A lights vapor fraction is removed overhead via line 3 and condensed in 4 with a portion refluxed via line 5 and the remainder recovered via line 6.

Purified product HEP is recovered via liquid side draw line 7 at an intermediate point and a heavier impurities steam is withdrawn as bottoms stream via line 8.

Figure 2:
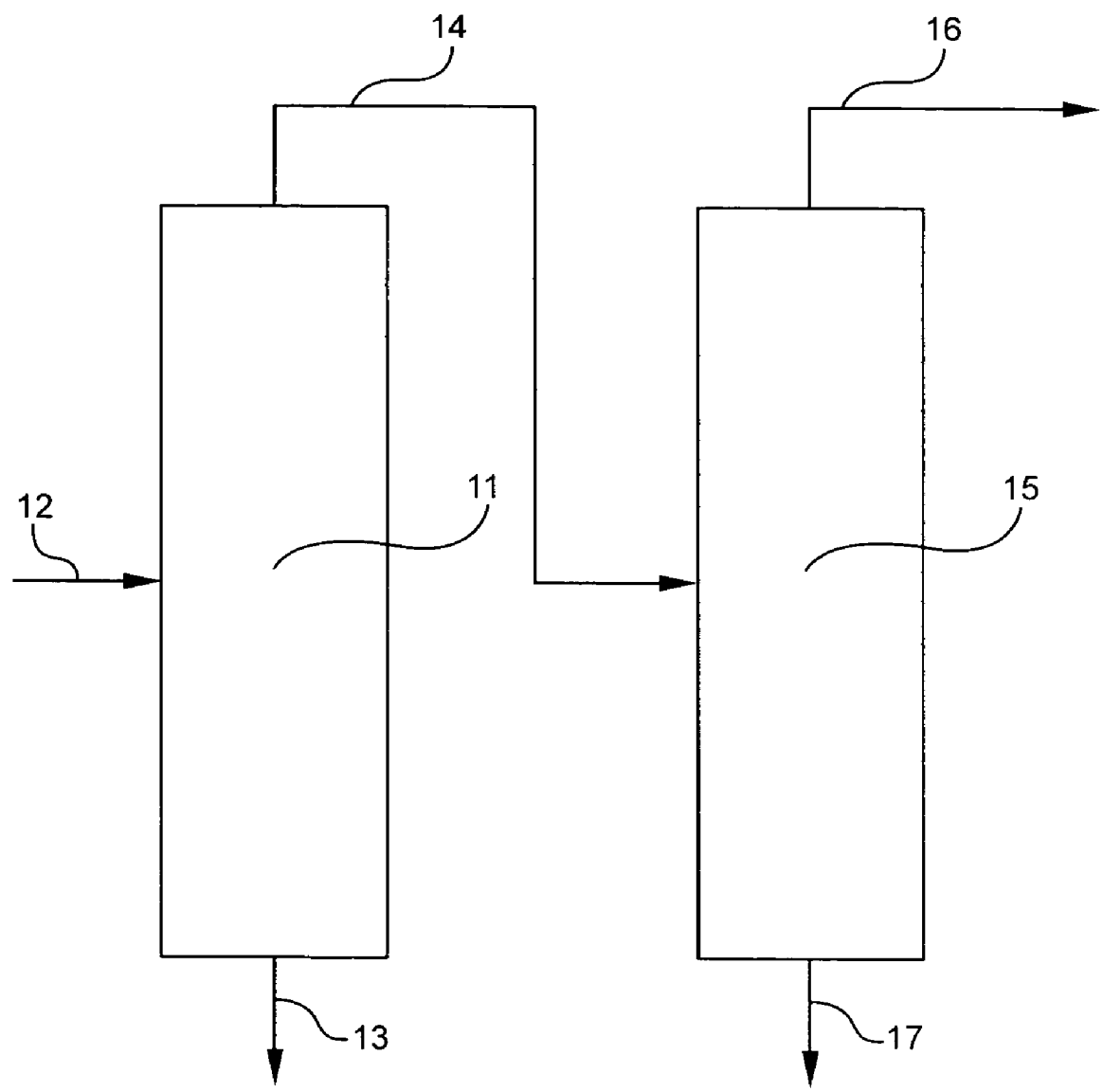
FIG. 2 schematically represents prior art procedures.

The product quality of the HEP recovered as shown in FIG. 1 is considerably better than that resulting from a two distillation column system as illustrated in FIG. 2 which is not in accordance with the invention. In the process of FIG. 2, the HEP containing reaction mixture is introduced into column 11 via line 12, a heavies bottom impurities steam is removed via line 13, and an overhead stream comprised of light impurities and HEP is removed via line 14 and passed to column 15. In column 15 a lights impurities stream is separated via line 16 and the product HEP stream is separated as bottoms via line 17.

The quality of the HEP product produced in accordance with the procedure of FIG. 2 is substantially inferior to that produced in accordance with the invention as described in FIG. 1 despite the provision of two distillation columns.

Figure 3:
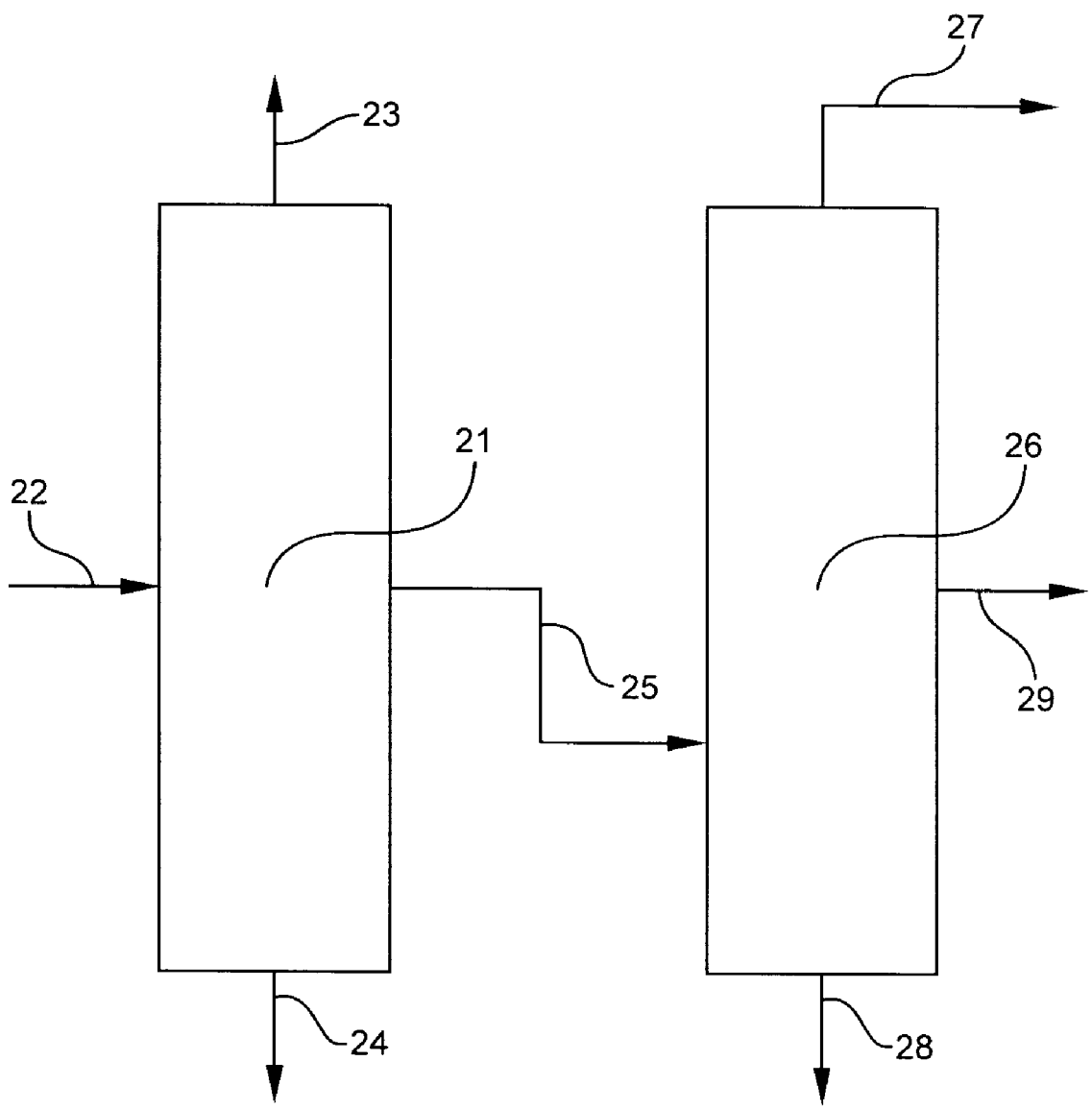
FIG. 3 schematically represents an alternative practice of the invention.

In carrying out the process of the invention, procedures which involve the use of more than one distillation column can be employed. FIG. 3 is illustrative.

Referring to FIG. 3, the HEP containing reaction mixture is introduced to column 21 via line 22 at an intermediate point. A lights impurity stream is removed overhead via line 23 and a liquid heavies impurities stream is separated via line 24. A stream concentrated in HEP is removed as a liquid side draw via line 25 and passes to column 26 wherein further distillation takes place. A lights impurities stream is separated overhead from column 26 via line 27 and a heavies bottom is separated via line 28. An intermediate product HEP stream is separated as side draw via line 29.

In the two columns configuration shown in FIG. 3, the further surprising discovery has been made that higher purity HEP product is recovered where the feed to column 26 is at a point which is below the line 29 product HEP side draw as depicted in FIG. 3. As will be seen from the working examples presented hereinafter, significantly better results are obtained in the case where feed to the second column is at a point below the sidestream product draw-off rather than at a higher point.

The invention can be illustrated by reference to the following examples.

EXAMPLE 1-1

Pass Sidedraw

The distillation column used was a 1" diameter glass Oldershaw column with a total of 35 trays. It had the condenser at the top and the reboiler at the bottom. The feed (crude HEP) entered the column at tray #5 (tray # is counted from top). The sidedraw was located at tray #25 (high sidedraw) or tray #35 (low sidedraw). The column was operated at 24-25 mm Hg on the top of the column with a reflux ratio of 0.5. The distilled HEP for example 1 was a mixture from the high and low sidedraws. The composition of the distilled HEP is shown in Table 1 and the dehydration result is shown in Table 2. Temperature profile was 230° C. at the reboiler, 223° C. at the sidedraw and 25° C. at the top.

EXAMPLE 2-2

Passes Overhead-Bottom without Sidedraws
(Comparative)

Same column as Example 1 except without sidedraws. For the first pass the crude HEP entered the column at tray

5 and the column was operated at 24-25 mm Hg on the top of the column. Reflux ratio was controlled at 0.5. The HEP and lighter components were removed from the top while the components heavier than HEP were removed from the bottom. The material recovered from the top of the column of the first pass distillation was then redistilled in the second pass distillation. The feed to the second pass distillation entered the column at tray #5 and the column was operated at 24-25 mm Hg. Reflux ratio was controlled at 0.5. The components lighter than HEP were removed from the top of the column while the purified HRP was recovered from the bottom of the column. The composition of the purified HEP is shown in Table 1 and the dehydration result is shown in Table 2. Temperature profile was 230° C. at the reboiler and 25° C. at the top for both passes.

EXAMPLE 3-2

Passes with Sidedraw, Low Feed Location on Second Pass

The distillation column was the same as Example 1. The first pass distillation was operated the same way as Example 1 with the sidedraw located at tray #25. The crude HEP entered the column at tray #5. The distilled HEP from the sidedraw of the first pass was then redistilled in the second pass. The feed to the second pass distillation entered the column at tray #35 (low feed) and the distilled HEP was recovered from the sidedraw which was located at tray #25. For both passes, the column was operated at 24-25 mm Hg on the top of the column and the reflux ratio was controlled at 0.5. The composition of the distilled HEP is shown in Table 1 and the dehydration result is shown in Table 2. The temperature profile was the same as Example 1.

EXAMPLE 4-2

Passes with Sidedraw, High Feed Location on Second Pass

This case is the same as Example 3 except the feed location for the second pass was at tray #5 instead of tray #35. The distilled HEP from the second pass was recovered from the sidedraw located at tray #25, same as Example 3. The composition of the distilled HEP is shown in Table 1 and the dehydration result is shown in Table 2. The temperature profile was the same as Example 1.

EXAMPLE 5-3

Passes Bottom-Overhead-Sidedraw

The distillation column in this case was a 40 mm diameter column with 3 sections of Sulzer CY packings. Each section was equivalent to 10 theoretical trays. Section 1 was the top section. Section 2 was the middle section. Section 3 was the bottom section.

For the first pass distillation, the crude HEP entered the column between Sections 1 and 2. The column was operated at 100 mm Hg on the top of the column with 50/1 reflux ratio. Water was removed from the overhead while components heavier than water were removed from the bottom. The temperature profile was 200° C. at the reboiler and 60° C. at the top.

For the second pass distillation, the bottom product from the first pass distillation entered the column between Sections 1 and 2. HEP and components lighter than HEP were removed from the top of the column while components heavier than HEP were removed from the bottom of the column. The column was operated at 25 mm Hg on the top of the column with 10/1 reflux ratio. The temperature profile was 220° C. at the reboiler and 190° C. at the top.

For the third pass distillation, the overhead product from the second pass distillation entered the column between Sections 1 and 2. Components lighter than HEP were removed from the top of the column while components heavier than HEP were removed from the bottom of the column. The purified HEP was recovered as a sidedraw product between Sections 2 and 3. The column was operated at 50 mm Hg with reflux ratio 10/1. The composition of the distilled HEP is shown in Table 1 and the dehydration result is shown in Table 2. The temperature profile was 217° C. at the reboiler, 213° C. at the sidedraw and 190° C. at the top.

The HEP product streams from the above examples had the following analysis as shown in Table 1.

TABLE 1

Composition of HEP

| | WT % | | | | |
|---|---|---|---|---|---|
| | Ex. 1 | Ex. 2 | Ex. 3 | Ex. 4 | Ex. 5 |
| HEP | 99.25 | 99.43 | 99.67 | 99.52 | 99.36 |
| MEA | 0.00 | 0.00 | 0.00 | 0.00 | 0.00 |
| GBL | 0.16 | 0.04 | 0.06 | 0.03 | 0.02 |
| BDO | 0.01 | 0.00 | 0.00 | 0.00 | 0.00 |
| 2-Py | 0.02 | 0.00 | 0.01 | 0.00 | 0.00 |
| HEHBA | 0.04 | 0.29 | 0.01 | 0.02 | 0.22 |
| AHP | 0.30 | 0.12 | 0.09 | 0.25 | 0.35 |
| Others | 0.20 | 0.12 | 0.16 | 0.18 | 0.05 |

Definitions
HEP N-[2-hydroxyethyl]-Pyrrolidone
MEA Monoethanol Amine
GBL gamma-Butyrolactone
BDO 1,4-Butanediol
2-Py 2-Pyrrolidone
HEHBA Hydroxyethyl hydroxybutyramide
AHP N-[3-aza-5-hydroxypentyl]-Pyrrolidone The product HEP streams were dehydrated to NVP in accordance with the following procedure.

Description of Dehydration Method

The unit was comprised of a feed pump to deliver HEP, a mass flow meter to deliver N2, a reactor U-tube heated with a sand bath and a glass receiver to collect the product. The reactor was a 1.25" OD, 0.97" ID 316SS tube. The entrance region above the catalyst bed was packed with glass beads. Immediately after the catalyst bed, the exit line was reduced to a 0.25" OD 316SS line to increase the linear velocity of the exit stream, allowing for recovery of the product. In addition to monitoring the temperature of the sand, a thermowell constructed of ¼" OD SS was placed in the center of the reactor to monitor the catalyst bed temperature. The reactor effluent was collected in a cold trap using an ice water bath to cool the receiver and analyzed using gas chromatography.

In a typical run, 10 cc of 1.6 wt % Cs/SiO2 catalyst (14/30 mesh) was loaded in the reactor. A feed of HEP in N2 (HEP WHSV=2.5/h, 10 mol % HEP in N2) was passed over the catalyst at 330° C. and atmospheric pressure. The results using HEP obtained by different distillation schemes are shown in Table 2.

TABLE 2

Dehydration Results

| Example | Distillation Scheme | % HEP Conversion after 50 h on stream | NEP Formation Rate* | % NVP Selectivity |
| --- | --- | --- | --- | --- |
| 1 | 1 pass sidedraw | 71.9 | 4.4 | 95.1 |
| 2 | 2 pass overhead - bottom | 73.9 | 13 | 96.7 |
| 3 | 2 pass sidedraw - sidedraw low feed | 77.0 | 1.8 | 97.0 |
| 4 | 2 pass sidedraw - sidedraw high feed | 66.0 | 8.7 | 94.9 |
| 5 | 3 pass bottom-overhead-sidedraw | 70.9 | 6.2 | 95.2 |

*increase in concentration of NEP (ppm) in NVP per hour.

An important characteristic of the HEP is the rate at which NEP is formed during dehydration. NEP (N-ethyl pyrrolidone) cannot be separated from NVP by distillation due to the closeness of the boiling points and thus for proper quality NVP the NEP content must be very low—Table 2 illustrates the significant reduction in NEP formation during dehydration with HEP prepared according to the invention.

As shown in the above working examples, superior quality HEP is produced as a result of the distillation sequence according to the invention. Although the overall HEP purity is similar to that obtained by comparative procedures, the key characteristic of HEP formation during dehydration is greatly improved through practice of the invention.

We claim:

1. In a process for separating purified N-(2-hydroxyethyl)-2-pyrrolidone from higher and lower boiling impurities by distillation in one or more distillation columns, the improvement which comprises separating high purity N-(2-hydroxyethyl)-2-pyrrolidone as a liquid distillation side stream without the N-(2-hydroxyethyl)-2-pyrrolidone having been separated as an overhead vapor stream at any point in the process.

2. In a process for separating purified N-(2-hydroxyethyl)-2-pyrrolidone from higher and lower boiling impurities using a single distillation column, the improvement which comprises separating purified N-(2-hydroxyethyl)-2-pyrrolidone as a liquid side stream from said lower and higher boiling impurities.

3. In a process for separating purified N-(2-hydroxyethyl)-2-pyrrolidone from higher and lower boiling impurities using two distillation columns the improvement which comprises separating an N-(2-hydroxyethyl)-2-pyrrolidone product stream as a liquid side stream in the first distillation column from higher and lower boiling impurities, feeding the separated N-(2-hydroxyethyl)-2-pyrrolidone stream to a second distillation column at an intermediate point and recovering purified N-(2-hydroxyethyl)-2-pyrrolidone from the second column as a liquid side stream.

4. The process of claim 3 wherein the feed to the second distillation column is at a point which is below the product N-(2-hydroxyethyl)-2-pyrrolidone side draw.

* * * * *